United States Patent
Guo et al.

(10) Patent No.: US 7,754,683 B2
(45) Date of Patent: Jul. 13, 2010

(54) BIOACTIVE PEPTIDE OF BONE MORPHOGENETIC PROTEIN-2

(76) Inventors: Xiaodong Guo, No. 1277, Jiefang Avenue, Hankou, Wuhan (CN) 430022; Qixin Zheng, No. 1277, Jiefang Avenue, Hankou, Wuhan (CN) 430022; Quan Yuan, No. 1277, Jiefang Avenue, Hankou, Wuhan (CN) 430022; Deyu Duan, No. 1277, Jiefang Avenue, Hankou, Wuhan (CN) 430022; Jianxiang Liu, No. 1277, Jiefang Avenue, Hankou, Wuhan (CN) 430022; Zhixia Duan, No. 1277, Jiefang Avenue, Hankou, Wuhan (CN) 430022

( * ) Notice: Subject to any disclaimer, the term of this patent is extended or adjusted under 35 U.S.C. 154(b) by 0 days.

(21) Appl. No.: 12/099,869

(22) Filed: Apr. 9, 2008

(65) Prior Publication Data

US 2009/0082272 A1 Mar. 26, 2009

Related U.S. Application Data

(63) Continuation of application No. PCT/CN2006/002780, filed on Oct. 19, 2006.

(30) Foreign Application Priority Data

Oct. 27, 2005 (CN) ............ 200510019679

(51) Int. Cl.
*A61K 38/00* (2006.01)
*A61K 38/16* (2006.01)
*A61K 38/18* (2006.01)

(52) U.S. Cl. ............ 514/2; 530/300; 530/324; 530/326; 514/12; 514/13; 514/7; 514/8

(58) Field of Classification Search ............ None
See application file for complete search history.

(56) References Cited

U.S. PATENT DOCUMENTS 6,495,129 B1 * 12/2002 Li et al. ............ 424/85.1

FOREIGN PATENT DOCUMENTS

EP 1288228 A1 * 3/2003

* cited by examiner

*Primary Examiner*—Elizabeth C. Kemmerer
(74) *Attorney, Agent, or Firm*—Matthias Scholl P.C.; Matthias Scholl

(57) ABSTRACT

A bone morphogenetic protein-2 active peptide is characterized in that the structure is $S^{[PO4]}$KIPKASSVPTELSAISTLYLDDD (SEQ ID NO: 1) or CCCCDDDS$^{[PO4]}$KIPKASSVPTELSAISTLYL (SEQ ID NO: 2) or $C^{16}H^{31}O$—NH—CCCCGGGS$^{[PO4]}$KIPKASSVPTELSAISTLYL (SEQ ID NO: 3). It overcomes the disadvantages of existing BMP-2, such as short half life, difficulty of sustained effect, complexity of equipments and preparation techniques, long production cycle, low yield, expensive price, and is accordingly difficult for large-scale production. In addition, the bone morphogenetic protein-2 active peptide exhibits the advantages, such as complete exposure of active sites, good ectopic osteogenesis ability, easy large-scale synthesis, lower cost, better stability and long duration. Meanwhile, the present invention also relates to the manufacturing method and application of such bone morphogenetic protein-2 active peptide.

2 Claims, 6 Drawing Sheets

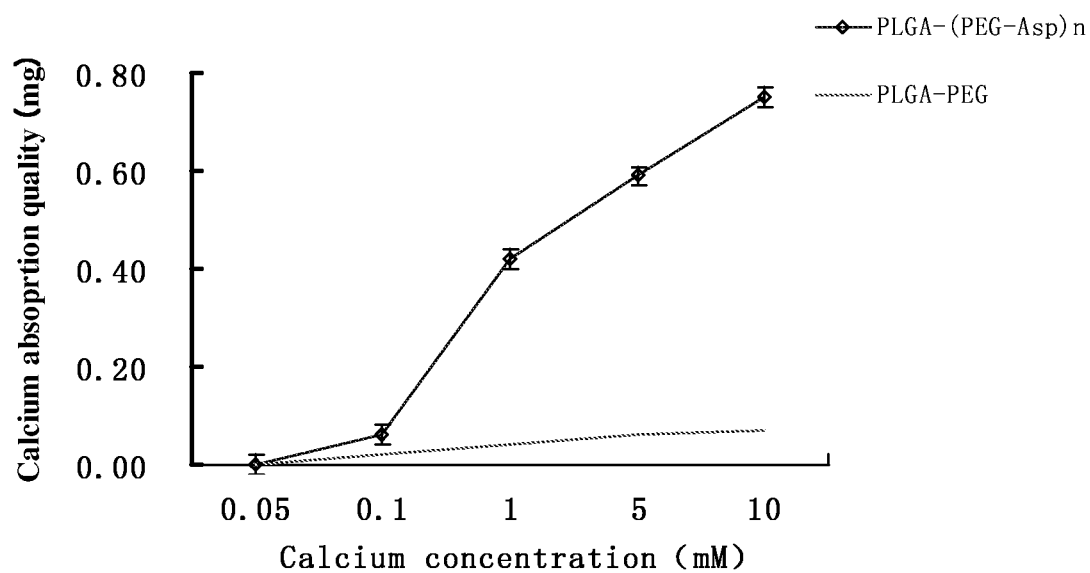
Fig.9
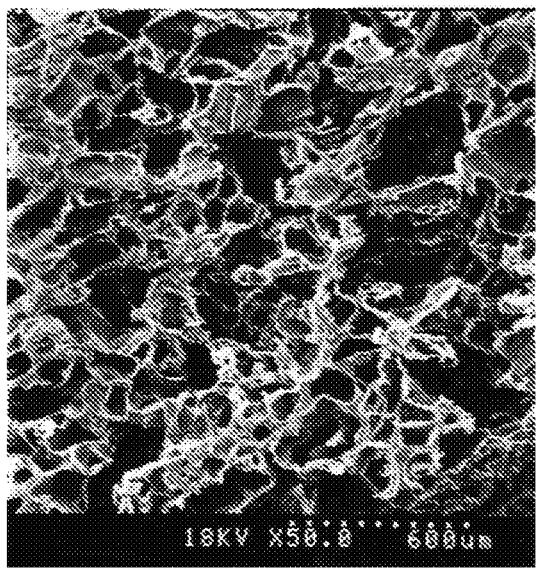
Fig. 10    Fig. 11

SEQUENCE LISTING

```
<160> NUMBER OF SEQ ID NOS: 4

<210> SEQ ID NO 1
<211> LENGTH: 24
<212> TYPE: PRT
<213> ORGANISM: Artificial Sequence
<220> FEATURE:
<223> OTHER INFORMATION: Synthetic Peptide, Synthesized by FMOC/tBu
      solid-state peptide synthesis
<220> FEATURE:
<221> NAME/KEY: MOD_RES
<222> LOCATION: (1)..(1)
<223> OTHER INFORMATION: PHOSPHORYLATION

<400> SEQUENCE: 1

Ser Lys Ile Pro Lys Ala Ser Ser Val Pro Thr Glu Leu Ser Ala Ile
1               5                   10                  15

Ser Thr Leu Tyr Leu Asp Asp Asp
            20

<210> SEQ ID NO 2
<211> LENGTH: 28
<212> TYPE: PRT
<213> ORGANISM: Artificial Sequence
<220> FEATURE:
<223> OTHER INFORMATION: Synthetic Peptide, Synthesized by FMOC/tBu
      solid-state peptide synthesis
<220> FEATURE:
<221> NAME/KEY: MOD_RES
<222> LOCATION: (8)..(8)
<223> OTHER INFORMATION: PHOSPHORYLATION

<400> SEQUENCE: 2

Cys Cys Cys Cys Asp Asp Asp Ser Lys Ile Pro Lys Ala Ser Ser Val
1               5                   10                  15

Pro Thr Glu Leu Ser Ala Ile Ser Thr Leu Tyr Leu
            20                  25

<210> SEQ ID NO 3
<211> LENGTH: 27
```

```
-continued

<212> TYPE: PRT
<213> ORGANISM: Artificial Sequence
<220> FEATURE:
<223> OTHER INFORMATION: Synthetic Peptide, Synthesized by FMOC/tBu
      solid-state peptide synthesis
<220> FEATURE:
<221> NAME/KEY: MOD_RES
<222> LOCATION: (1)..(1)
<223> OTHER INFORMATION: C16H31O- MODIFIED
<220> FEATURE:
<221> NAME/KEY: MOD_RES
<222> LOCATION: (7)..(7)
<223> OTHER INFORMATION: PHOSPHORYLATION

<400> SEQUENCE: 3

Cys Cys Cys Gly Gly Gly Ser Lys Ile Pro Lys Ala Ser Ser Val Pro
1               5                   10                  15

Thr Glu Leu Ser Ala Ile Ser Thr Leu Tyr Leu
            20                  25

<210> SEQ ID NO 4
<211> LENGTH: 20
<212> TYPE: PRT
<213> ORGANISM: Artificial Sequence
<220> FEATURE:
<223> OTHER INFORMATION: Synthetic Peptide, Derived from the bone
      morphogenetic protein-2 knuckle epitope

<400> SEQUENCE: 4

Lys Ile Pro Lys Ala Ser Ser Val Pro Thr Glu Leu Ser Ala Ile Ser
1               5                   10                  15

Thr Leu Tyr Leu
            20
```

BIOACTIVE PEPTIDE OF BONE MORPHOGENETIC PROTEIN-2

CROSS-REFERENCE TO RELATED APPLICATIONS

This application is a continuation of International Patent Application No. PCT/CN2006/002780 with an international filing date of Oct. 19, 2006, designating the United States, now pending, and further claims priority benefits to Chinese Patent Application No. 200510019679.X, filed on Oct. 27, 2005. The contents of these specifications are incorporated herein by reference.

BACKGROUND OF THE INVENTION

1. Field of the Invention

The present invention relates to the clinical medicine field, especially to a bone morphogenetic protein-2 active peptide. The present invention also relates to a method for manufacturing the active peptide and the application on medicine for promoting osteogenesis and repairing bone defect.

2. Description of the Related Art

According to statistics, there are 3 million patients suffering from bone defect or bone injury due to various factors, such as traffic, production safety accident and bone disease, associated with the increasing trend year by year. Thus, the demand of substantial bone repair materials is urgent, and the market is huge. With the advancement of technology, via the implementation of clinical autologous or allogeneic tissue transplantation and the use of synthetic bone tissue substitutes, great progress has been made on the treatment of these diseases. However, there also exist the disadvantages that are the expense of individual normal tissues, the shortage of donor source, expensive price, and the problems of rejection and secondary infection, which could not meet clinical requirements. At present, how to fundamentally solve the repair of bone defects has become the international medical leading issue.

In recent years, the use of tissue engineering techniques, namely via composite transplantation or separate implantation of extracellular matrix materials, cell growth factors and seed cells to repair bone defects, has drawn many countries' great attention. However, corresponding researches about bones at home and abroad are still at the beginning stage, accordingly many problems remain to be solved, in which one of key problems is how to develop remarkable medicines or materials of repairing bone defects.

Bone morphogenetic proteins, namely BMPs for abbreviation, are glycoprotein polypeptides in bone matrix, which include the disulfide bond structure. Bone morphogenetic proteins, the relative molecular mass being 18000-30000, constitute a peptide factor family exhibiting similar structure and functions expect BMP-1. So far, 43 kinds of bone morphogenetic proteins in the family have been found. Bone morphogenetic protein is the only local growth factor that can solely induce the formation of bone tissue, inducing undifferentiated mesenchymal cells in vivo into cartilage and bone. Bone morphogenetic proteins exhibit different abilities of induced osteogenesis, in which bone morphogenetic protein-2 has been studied extensively and has greatest osteogenesis ability.

However, BMP-2 is a powder-efficient material, which could not be evenly distributed in the bone defects and exhibits no function of supporting. Moreover, BMP-2 has a short half life in vivo and metabolizes quickly when local application. Thus, relative high dose is essential to stimulate sufficient osteogenesis for persistent therapy effect. Accordingly, clinical therapy cost would increase, and it is possible to cause toxicity. Large-scale production of BMP-2 and more wide clinical application have always been difficult for current research.

At present, techniques such as molecular biology and genetic engineering are used at home and abroad for production of recombinant human bone morphogenetic protein-2 (rhBMP-2). However, due to complexity of equipments and preparation techniques, long production cycle, low yield and expensive price, it is difficult to achieve large-scale production, and also exists safety problems of genetic engineering products (Wozney J, Seeherman H. Protein-based tissue engineering in bone and cartilage repair. Curr Opin Biotechnol, 2004, 15(5): 392-398.). For clinical application, inorganic materials, polymers, biological materials, composite materials and the like are used as BMP-2 or rhBMP-2 vectors for treatment. Nevertheless, for various materials, there are differences in many aspects, such as biocompatibility, mechanical property, osteoconductivity, osteoinductivity, plasticity and degradability. But there are still no substitutes for bone tissues, which can meet the requirements of perfect materials of repairing bone defects. In this way, the applications of extrinsic BMP2 or rhBMP-2 on fracture therapy are limited. In addition, macromolecular proteins would randomly enfold when adhered to material surfaces, so that the bioactivity is not high because of insufficient exposure of active sites.

Another method is to transfer BMP-2 gene into mesenchymal stem cells using transgene technology and express BMP-2 by transgenic cell. As the recent reports described, vectors of bone morphogenetic protein-2 gene are mostly adenovirus, in which virus vectors could cause harm to hosts through persistent proliferation. For host genes, the mutation risk also exists due to the intervention of extrinsic genes; extrinsic genes, transferred by non-virus vectors, would not be integrated into chromosomes of host cells, not causing excessive expression and deactivation of genes on entry sites. Thus, there is no insertion mutation risk, but less efficient expression. In addition, the time and quantity of gene expression in vivo could not be artificially controlled. But there are still disadvantages such as low transfection efficiency, short expression and potential carcinogenicity of virus vectors. (Chadderdon R, Shimer A, Gilbertson L. Advances in gene therapy for intervertebral disc degeneration. Spine J. 2004, 4 (6 Suppl): 341S-34.). Therefore, gene therapy on the basis of BMP-2 is still far from clinical application.

SUMMARY OF THE INVENTION

In view of the disadvantages in the prior art, one objective of the invention is to provide a bone morphogenetic protein-2 active peptide.

Another objective of the present invention is to provide a method for manufacturing the bone morphogenetic protein-2 active peptide.

Again another objective of the present invention is to provide a application of bone morphogenetic protein-2 active peptide of the invention to medicine preparation for promoting osteogenesis and repairing bone defect The purposes of the present invention can be achieved as follows:

The structure of a bone morphogenetic protein-2 active peptide is $S^{[PO_4]}$IPKASSVPTELSAISTLYLDDD (bone morphogenetic protein-2 active peptide 1) (SEQ ID NO: 1); or CCCCDDDS$^{[PO_4]}$KIPKASSVPTELSAISTLYL (bone morphogenetic protein-2 active peptide 2) (SEQ ID NO: 2);

or C$_{16}$H$_{31}$O—NH—CCCCGGG S$^{[PO4]}$—KIPKASSVP-TELSAISTLYL (bone morphogenetic protein-2 active peptide 3) (SEQ ID NO: 3).

The preparation method of bone morphogenetic protein-2 active peptide mentioned above is:

BMP-2 receptor II in the amino acid sequence of BMP-2 exhibits many epitopes. The characteristic "knuckle epitope" (Kirsch T, Sebald W, Dreyer M K. Crystal structure of the BMP-2-BRIA ectodomain complex. Nat Struct Biol, 2000, 7(6): 492-496.) exhibits the core functional region of induced osteogenesis, in which the amino acid sequence is "KIP-KASSVPTELSAISTLYL" (SEQ ID NO: 4) (Saitoa A, Suzuki Y, Ogataa 5, et al. Activation of osteo-progenitor cells by a novel synthetic peptide derived from the bone morphogenetic protein-2 knuckle epitope. Biochimica et Biophysica Acta, 2003, 1651: 60-67.).

By adding a phosphorylated senile to one end and three aspartates to another end, the bone morphogenetic protein-2 active peptide 1 (S$^{[PO4]}$KIPKASSVPTELSAISTLYLDDD) (SEQ ID NO: 1 is formed.

Or, adding four cysteines, three aspartates and a phosphorylated serine to one end, the formation of bone morphogenetic protein-2 active peptide 2 (CCCCDDDS$^{[PO4]}$KIP-KASSVPTELSAISTLYL) (SEQ ID NO: 2) can be achieved;

Or, adding four cysteines, three glycins, and a phosphorylated serine to one end, the cysteine on the end-to-side polypeptide chain modified by palmitic acid ester (C$_{16}$H$_{31}$O—), a bone morphogenetic protein-2 active peptide 3 (C$_{16}$H$_{31}$O—NHCCCCGGGS$^{[PO4]}$—KIPKASSVPTEL-SAISTLYL) (SEQ ID NO: 3) is formed.

Three peptides are synthesized by conventional FMOC/tBu solid-phase peptide synthesis (Barany G, Merrifield R B. 1979. Solid phase peptide synthesis. In: Gross E, Meienhofer J. eds. The peptides uol2. New York Academic Press. pp 1-284.):9-fluorenylmethoxycarbonyl (Fmoc), unstable to alkali, is used for protecting the α-amino of amino acids; tert-butyl or other protective groups, unstable to alkali, is used for protecting side-chain functional groups of amino acid; polyamide resin is used for peptide synthesis of solid-phase carrier. Thus, after purification through gel chromatography and purity analysis by HPLC, crude peptides are gained through freezing.

These three peptides can significantly simulate the functions of stimulating natural bone matrix and guiding biomineralization and make local environment acid. Then, they could facilitate self-assembly deposition of local calcium and phosphorus on the collagen fiber surface of local tissue in vivo to grow into the hard and micro crystal structure of hydroxyapatite, in which the structure is arranged as the same direction and is very similar to natural bone structure. Thus, it can function similar to natural BMP-2.

Compared to common bone morphogenetic protein medicines, the active peptides exhibit the advantages as follows: (1) the active peptides can play a similar role as proteins, and active sites of short-chain peptides can be fully exposed and bound with the corresponding receptors on cell surface to achieve better bioactivity. The experimental results show that the active peptides exhibit good ectopic osteogenesis ability (see experimental research on animal ectopic osteogenesis in the manual); (2) two ends of the active peptide sequence contain phosphorylated serine, cysteine (two amino acids are polar neutral amino acids) and aspartate (it is acidic amino acid). When peptides are bound with corresponding matrix materials, these amino acids in two ends can form anionic active groups, such as phosphate and carboxyl, on the material surface in simulated body fluid. These anionic active groups, strongly affinitive to calcium and phosphorus, are important functional sites for stimulating and guiding mineralization. They can promote calcium and phosphorus deposition, crystal nucleation and self-assembled mineralization to control the function of self-assembly mineralization in vivo. Active peptides have better osteoinductive activity because of the existence of these neutral and acidic amino acids, promoting the effectiveness of osteoblasts. Our research indicates that anionic active groups, such as phosphate, could further promote the matrix material mineralization (see experimental research on material biomineralization in the manual); (3) small peptide is usually referred to the composition of less than 100 amino acids, while more than 100 amino acids constitute a protein. Small peptide, composed of less than 50 amino acids, can be artificially synthesized in an easy way, but the synthesis of peptides, composed of more than 50 amino acids or protein, is difficult and thereby expressed by genetic engineering. Compared to bone morphogenetic proteins, small peptides exhibit smaller structure, and are easier for large-scale synthesis. Thus, economic burden of patients suffering from bone defect is significantly reduced because of less cost. (4) due to small relative molecular mass of peptides, the formulation is more abundant. First, peptides can be made into solution, and directly injected in the regions of bone defect or nonunion. Second, peptides are packed using polymeric material microsphere by microsphere coated technology so as to achieve sustained release effect after implantation in vivo; Third, water soluble peptides can be introduced to the PLA or PCL chain to synthesize a new copolymer that is biodegradable. The copolymer exhibits biological functions, and can be implanted into lesion regions for treatment; (5) Research shows that small peptide hormones can cause different aging positive or negative physiological activities and biochemical reaction regulation. The activity is extremely high, so that only a very small dose (1/million grams) can induce significant body reaction. The peptides exhibit better stability in the composite process of matrix material, and afterward would release along with gradual degradation of material itself. The longer duration could achieve sustained release effect to promote bone defect repair better and faster.

BRIEF DESCRIPTION OF THE DRAWINGS

FIG. 9 is the quality analysis result of calcium absorption, FIG. 10 is the PLGA-(PEG-ASP)$_n$ scaffold material displayed by SEM (×50), FIG. 11 is the PLGA-(PEG-ASP)$_n$ scaffold material in simulated body fluid on the eighth day displayed by SEM (×2000)

DETAILED DESCRIPTION OF THE INVENTION

Figure 1:
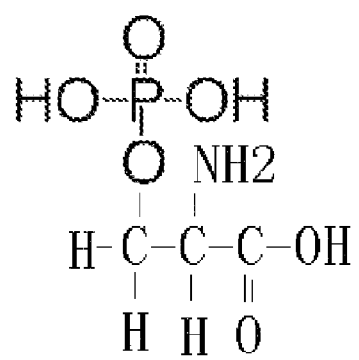
FIG. 1 is a chemical structure of phosphorylated serine.
Figure 2:
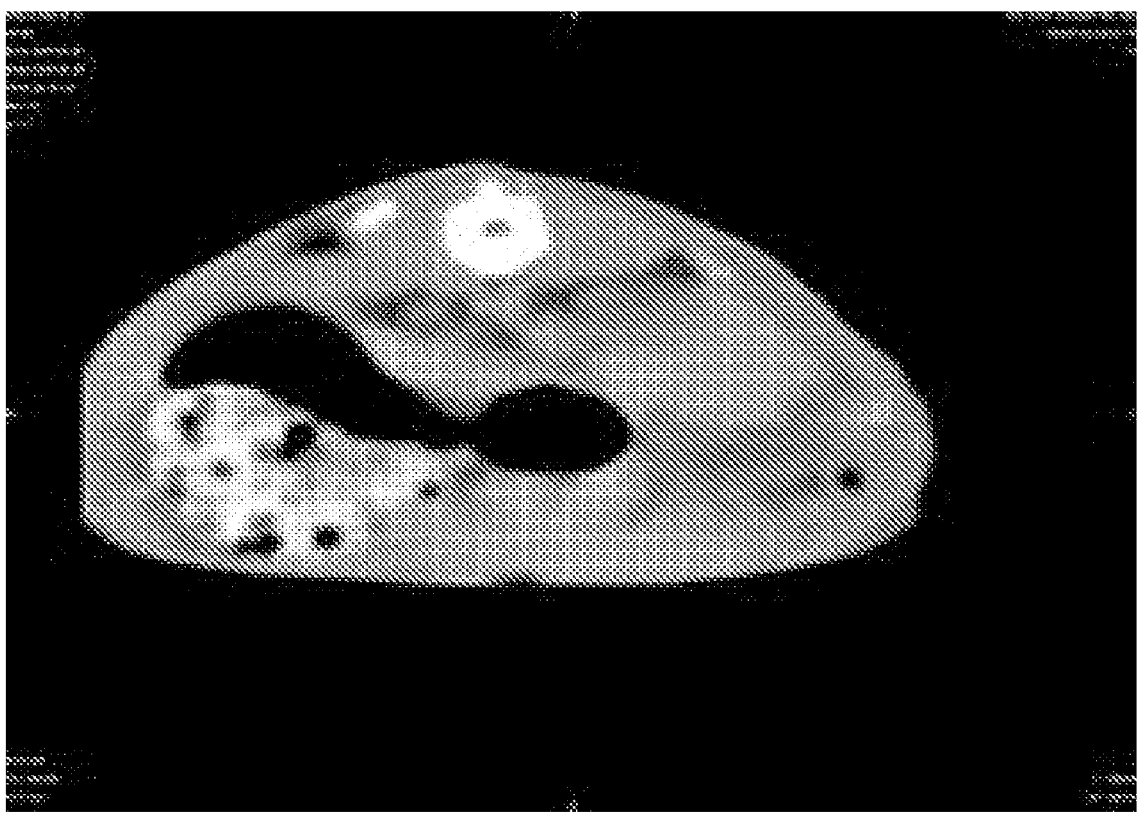
FIG. 2 is a CT photo of ectopic osteogenesis of bone morphogenetic protein-2 active peptide 1 in Wistar rats.
Figure 3:
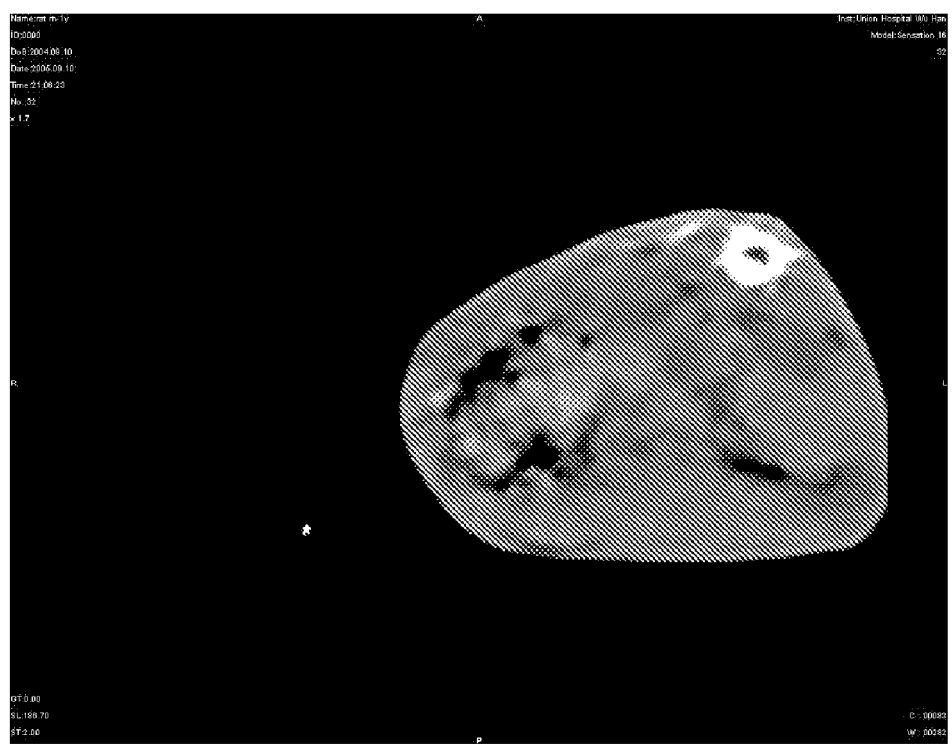
FIG. 3 is a CT photo of ectopic osteogenesis of bone morphogenetic protein-2 active peptide 2 in Wistar rats.
Figure 4:
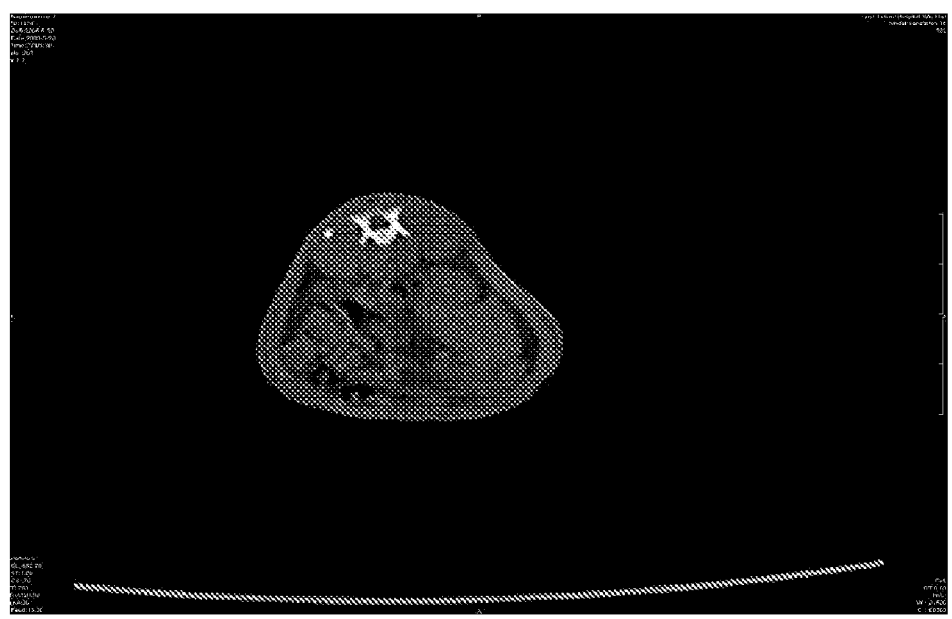
FIG. 4 is a CT photo of ectopic osteogenesis of bone morphogenetic protein-2 active peptide 3 in Wistar rats.
Figure 5:
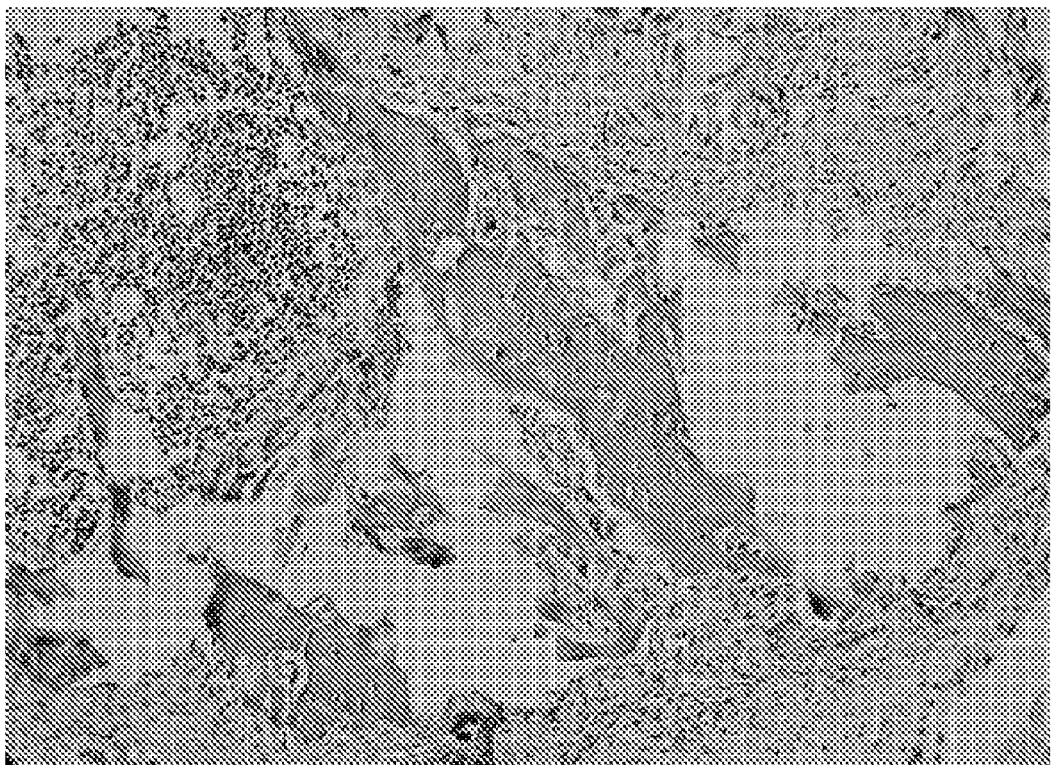
FIG. 5 is a HE staining slice figure of ectopic osteogenesis of bone morphogenetic protein-2 active peptide 1 after 8 weeks under a optical microscope (×10)
Figure 6:
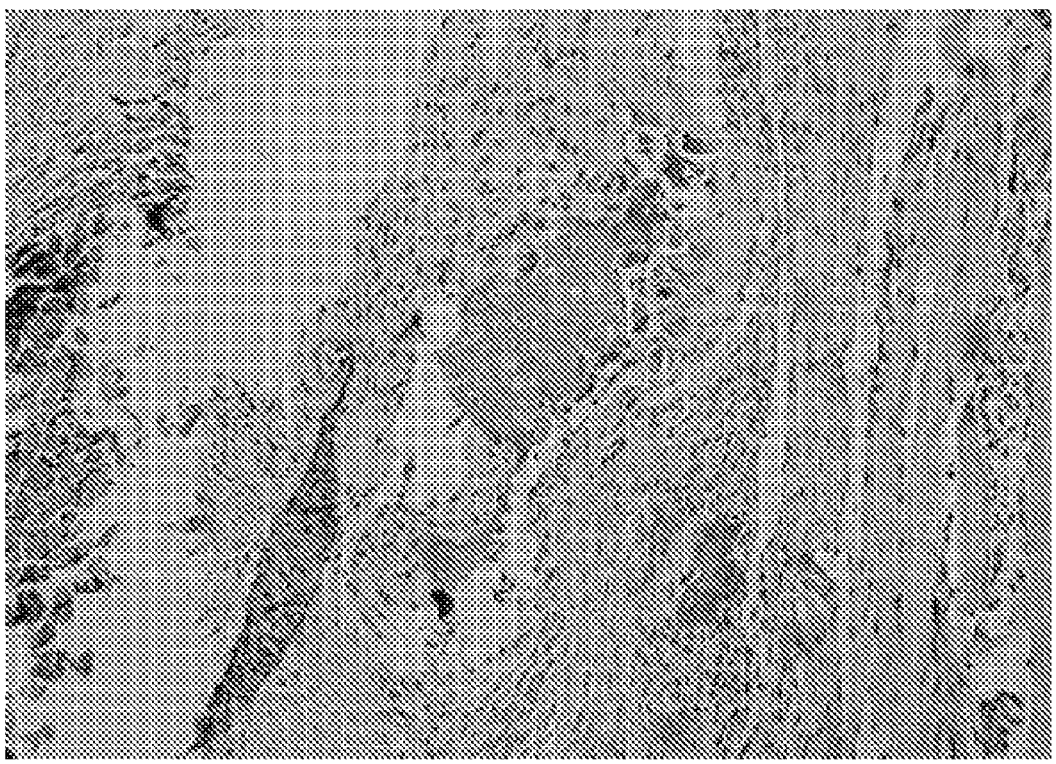
FIG. 6 is a HE staining slice figure of ectopic osteogenesis of bone morphogenetic protein-2 active peptide 2 after 8 weeks under a optical microscope (×10)
Figure 7:
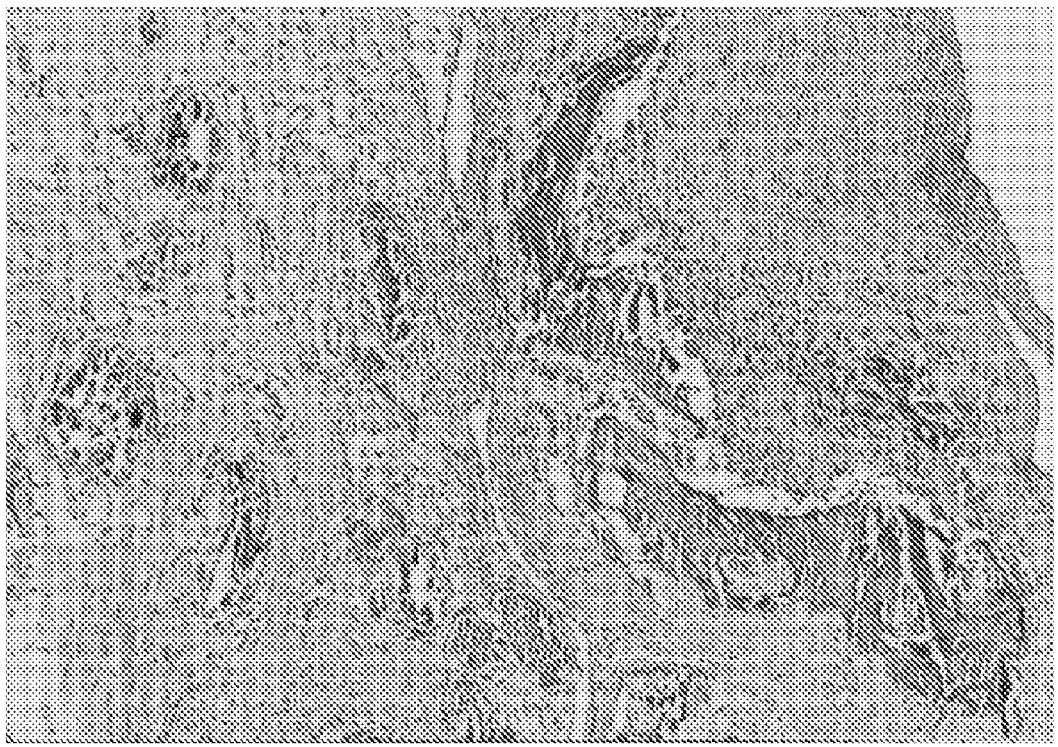
FIG. 7 is a HE staining slice figure of ectopic osteogenesis of bone morphogenetic protein-2 active peptide 3 after 8 weeks under a optical microscope (×10)
Figure 8:
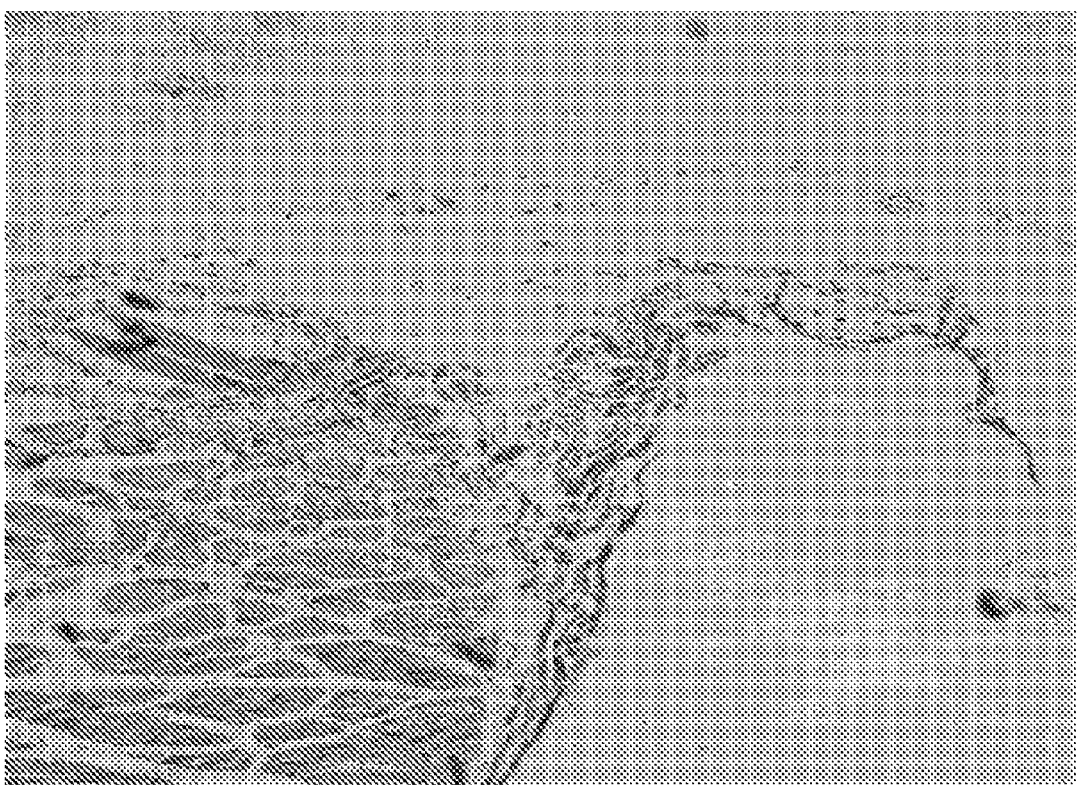
FIG. 8 is a HE staining slice figure of placement into pure collagen sponge material site after 8 weeks under a optical microscope (×10)

Further exemplary embodiments and advantages of the present invention are explained below by reference to the drawings: FIGS. 2, 3, 4, 5, 6, 7 and 8 are the results of animal experiments, that are imaging and histological test figures of ectopic osteogenesis after bone morphogenetic protein-2 active peptide 1, 2, 3 placed into Wistar rats. FIGS. 9, 10, 11, 12, 13 and 14 are result figures of matrix material biomineralization experiments.

1) Experimental Research on Animal Ectopic Osteogenesis:

(1) Material Preparation:

Bone morphogenetic protein-2 active peptide 1 ($S^{[PO4]}$KIPKASSVPTELSAISTLYLDDD) (SEQ ID NO: 1), bone morphogenetic protein-2 active peptide 2 (CCCCDDDS$^{[PO4]}$KIPKASSVPTELSAISTLYL) (SEQ ID NO: 2) and bone morphogenetic protein-2 active peptide 3 ($C_{16}H_{31}O$—NH—CCCCGGGS$^{[PO4]}$KIPKASSVPTELSAISTLYL) (SEQ ID NO: 3) are respectively synthesized by FMOC/tBu solid-phase peptide synthesis.

The used collagen sponge is the product of Wuhan boster company.

The scaffold material is collagen sponge, the size of which is 5×5×5 mm³. Three bone morphogenetic protein-2 active peptides are dissolved into saline solution, and then dropped on the collagen sponge in accordance with the 0.4 mg dose. Meanwhile, equivalent saline solution is dropped on the control pure collagen sponge, and freeze-dried for reserve after complete absorption.

(2) groups: 36 Wistar rats are randomly divided into three experimental groups, namely 0.4 mg bone morphogenetic protein-2 active peptide 1/collagen sponge group, 0.4 mg bone morphogenetic protein-2 active peptide 2/plastic Sponge group and 0.4 mg bone morphogenetic protein-2 active peptide 3/collagen sponge group, and the control group is using pure collagen sponge.

(3) Implantation of Peptide/Collagen Sponge and Pure Collagen Sponge:

The anesthesia of rats is achieved by ketamine intraperitoneal injection. For two experimental groups, 0.4 mg bone morphogenetic protein-2 active peptide 1/collagen sponge and 0.4 mg bone morphogenetic protein-2 active peptide 2/collagen sponge are respectively implanted with 1 cm incision in the sacral spine muscles on the back. For 0.4 mg bone morphogenetic protein-2 active peptide 3/collagen sponge group, pure collagen sponge of the same size is implanted into the gaps along one side of sacral spine muscles. CT radiography inspection of three rats groups is done after implantation in the 3, 6, 8 weeks, and then four rats of each group are killed at each time point. Local tissues of implant materials are sampled, after fixation by formaldehyde and paraffin-embedded sections, and histological observation is done with HE staining.

CT scan imaging of experimental results shows that significant ectopic osteogenesis occur in animals, into which bone morphogenetic protein-2 active peptide 1, 2, 3 are placed (FIG. 2, FIG. 3, FIG. 4); histological examination (FIG. 5) shows that significant formation of new bone occur in the eighth week for bone morphogenetic protein-2 active peptide 1/collagen sponge group, associated with full development, and the majority of new bone is continuous. Histological examination (FIG. 6) shows that significant formation of new bone occur in the eighth week for bone morphogenetic protein-2 active peptide 2/collagen sponge group. Furthermore, there are visible active bone cells, arrayed in rows, on the surface of wide trabecular bone. Histological examination (FIG. 7) shows that significant formation of new bone occur in the eighth week for bone morphogenetic protein-2 active peptide 3/collagen sponge group, associated with full development. For pure collagen sponge group, there are just fiber tissue formation and no osteoid formation, associated with complete degradation and absorption of fiber until the eighth week.

The experimental results show that bone morphogenetic protein-2 active peptide 1, bone morphogenetic protein-2 active peptide 2 and bone morphogenetic protein-2 active peptide 3 exhibit good ectopic osteogenesis ability. In addition, bone morphogenetic protein-2 exhibits similar osteogenic activity, which has broad application value in bone tissue engineering field.

2) Experimental Study of Matrix Material Biomineralization (1) Material Preparation:

The synthesis of polymeric materials lactide/glycollide/aspartic acid-polyethylene glycol (English name is PLGA-(PEG-ASP)n) multicopolymer: lactide (DLLA), glycollide (GA) and aspartic acid-polyethylene prepolymers are synthesized by ring-open polymerization. Materials are made into circular sheets of 5 mm diameter and 2 mm thickness.

Polymeric material poly(lactide-co-glycollide)-polyethylene glycol (English name is PLGA-PEG) is made into circular sheets of 5 mm diameter and 2 mm thickness.

(2) Adsorption Quality Analysis of Calcium:

40 sheets of two polymeric materials are divided into 5 groups, put into 24-well plates containing NaCl buffer solution of different calcium concentration (PH=7.4, 150 mM), and placed under 37° C. The calcium concentration of each group is respectively 0.05, 0.1, 1, 5 and 10 mM. After 48 hours, by measuring the residual amount of calcium in solution, the calcium content adsorbed on each scaffold material is obtained. The calcium concentration in solution was measured by colorimetric analysis.

(3) Biomineralization

Place PLGA-(PEG-ASP)$_n$ and PLGA-PEG scaffold materials into 24-well tissue culture dishes, and add 15 ml improved simulated body fluid into each well, which are placed respectively at 0, 4, 8, 12, 16 days. Change fresh simulated body fluid every day to ensure adequate ion concentrations. The composition of improved simulated body fluid is: $H_2O$: 141 mM NaCl, 4.0 mM KCl, 0.5 mM $MgSO_4$, 1.0 mM $MgCl_2$, 4.2 mM $NaHCO_3$, 5.0 mM $CaCl_2$, and 2.0 mm $KH_2PO_4$.

The solution after synthesis is cushioned with a Tris-HCl solution to pH=6.8 buffer. Each material in each culture period before and after treatment is freeze-dried for scanning electron microscope observation and quality inspection.

(4) Experimental Result and Analysis

The analysis result of calcium absorption quality shows: the calcium absorption quality on the PLGA-PEG material is significantly less than the calcium absorption quality on the PLGA-(PEG-ASP)$_n$ material. In addition, calcium absorption amount on two materials both increase as the increase of calcium ion concentration in solution (FIG. 9).

Figure 12:
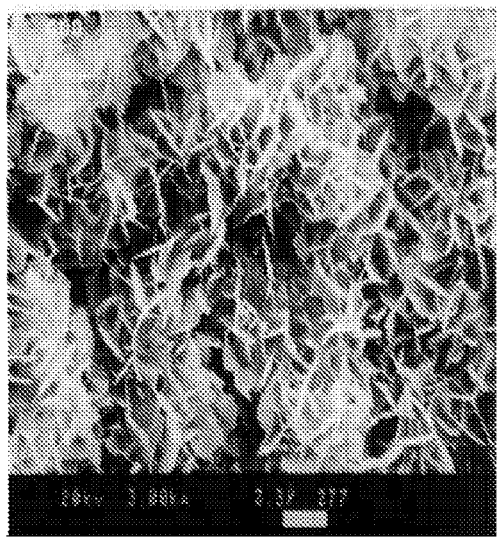
FIG. 12 is the PLGA-(PEG-ASP)$_n$ scaffold material in simulated body fluid on the sixteenth day displayed by SEM (×3000)
Figure 13:
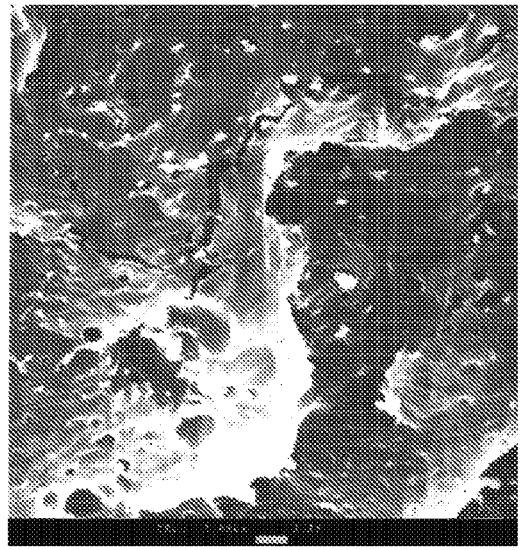
FIG. 13 is the PLGA-PEG scaffold material in simulated body fluid on the sixteenth day displayed by SEM (×3000)
Figure 14:
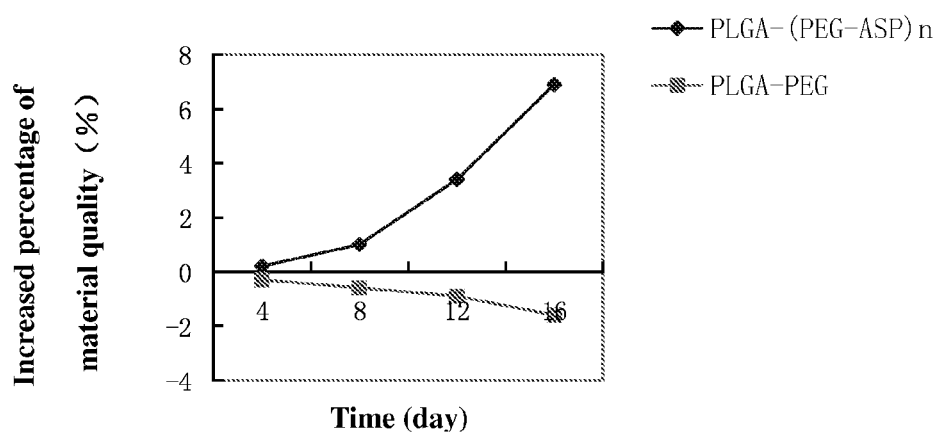
FIG. 14 is the quality test result of PLGA-(PEG-ASP)$_n$ material and PLGA-PEG scaffold material at each time point.

The biomineralization result shows SEM images of PLGA-(PEG-ASP)$_n$ copolymer scaffold material before treatment (FIG. 10). In different culture periods, SEM shows that continuous nucleation and growth of low crystal hydroxyapatite nano-crystals, full of carbon dioxide, occur in the internal porous structure of PLGA-(PEG-ASP)$_n$ copolymer scaffold materials. With the extended culture period, the precipitation scope of biominerals in the internal porous structure significantly extends. After 8 days, many independent mineralization crystals in the internal porous structure of materials grow (FIG. 11). After 16 days, a continuous mineralization layer is formed, and biomineralization crystals display thin sheet structure (FIG. 12). There is no significant mineral growth in various culture periods on the surface of PLGA-PEG scaffold materials (FIG. 13). Quality test results show that the quality of PLGA-(PEG-ASP)$_n$ materials improves significantly as the increase of time, associated with no significant change of PLGA-PEG scaffold group in the quality (FIG. 14).

At present, polyethylene glycol (PEG) is generally used to trigger lactide and glycollide copolymer to improve the hydrophilicity of PLGA. However, lacking functional groups in the block copolymer, it is difficult to achieve further composition with bioactive molecules and significant improvement on the affinity of cell. In addition, the ability of nucleation and self-assembly mineralization, as well as induced calcium and phosphorus deposition, is not good. We induct amino acid sequences containing active group into the PLGA-PEG block copolymer in order to improve the defects of such copolymer due to lack of functional groups, which has been reported in the past.

The experimental results show that the modification of amino acid sequences by active group could produce differences in surface chemistry, which could significantly influence calcium adsorption on the multicopolymer scaffold. PLGA copolymers, modified by aspartic acid-polyethylene glycol prepolymer, have abundant functions of anionic groups. These anionic groups in vivo are important functional sites of promotion and guidance of mineralization. Moreover, they have a strong affinity to calcium and phosphorus to promote the deposition of calcium and phosphorus, crystal nucleation and self-assembled mineralization, functioning to control biological self-assembly mineralization of the body.

What is claimed is:

1. A bone morphogenetic protein-2 active peptide consisting of amino acid sequence of formula S$^{[PO4]}$KIPKASSVPTELSAISTLYLDDD (SEQ ID NO: 1), or of formula CCCCDDDS$^{[PO4]}$KIPKASSVPTELSAISTLYL (SEQ ID NO: 2), or of formula C$_{16}$H$_{31}$O—NH—CCCGGGS$^{[PO4]}$KIPKASSVPTELSAISTLYL (SEQ ID NO: 3, wherein said peptide has osteoinductive activity and is capable of promoting bone regeneration and repair of bone defects.

2. An osteoinductive composition comprising the peptide of claim 1 and a physiologically acceptable diluent, carrier, or excipient.

* * * * *